(12) United States Patent  
Scampini

(10) Patent No.: US 7,344,506 B2  
(45) Date of Patent: Mar. 18, 2008

(54) CELL COLLECTION DEVICE

(75) Inventor: Steven A. Scampini, Groton, MA (US)

(73) Assignee: Cytyc Corporation, Marlborough, MA (US)

( * ) Notice: Subject to any disclaimer, the term of this patent is extended or adjusted under 35 U.S.C. 154(b) by 0 days.

(21) Appl. No.: 11/725,846

(22) Filed: Mar. 20, 2007

(65) Prior Publication Data

US 2007/0173737 A1  Jul. 26, 2007

Related U.S. Application Data

(62) Division of application No. 11/314,754, filed on Dec. 21, 2005, now abandoned.

(51) Int. Cl.  
*A61B 10/00* (2006.01)

(52) U.S. Cl. ..................... 600/572; 600/569

(58) Field of Classification Search .......... 600/562, 600/569–573, 580; 422/99, 100  
See application file for complete search history.

(56) References Cited

U.S. PATENT DOCUMENTS 3,792,699 A * 2/1974 Tobin et al. ............. 600/572  
4,875,602 A * 10/1989 Chickering et al. ....... 222/187  
6,988,892 B2 * 1/2006 Dragan et al. ............ 433/90

* cited by examiner

*Primary Examiner*—Max Hindenburg  
*Assistant Examiner*—Jonathan M Foreman  
(74) *Attorney, Agent, or Firm*—Mark J. Casey; Theodore Allen

(57) ABSTRACT

This invention relates generally to medical devices, and more particularly, an apparatus and method for collecting cells or tissue samples from the cervix of a patient for medical testing.

5 Claims, 2 Drawing Sheets

CELL COLLECTION DEVICE

CROSS REFERENCES TO RELATED APPLICATIONS

This application is a divisional of U.S. patent application Ser. No. 11/314,754 filed on Dec. 21, 2005 now abandoned. The full disclosures of the prior applications of which are incorporated herein by reference in their entirety.

FIELD OF THE INVENTION

This invention relates generally to medical devices, and more particularly, an apparatus and method for collecting cells or tissue samples from the cervix of a patient for medical testing.

BACKGROUND OF THE INVENTION

Cancer is responsible for significant health problems in populations of women in the United States and throughout the world. In particular, gynecological cancers, including ovarian, uterine, cervical, and vuvlar cancers, are responsible for over 5,000 deaths in the United States each year. Although recent years have seen advances in detection and treatment of these cancers, mortality rates remain significantly high.

Cervical cancer can be prevented and possibly cured if detected early enough in its precancerous or precursor stages. There are a variety of known techniques for the early detection of cervical cancer. Most of these techniques include the scraping or sampling of tissue from the uterine or endocervical canal using a spatula or brush collection device. Tissues or cells obtained with these devices would be subjected to cytological or other examinations, such as the Papanicolaou or Pap smear.

The present invention relates to an improved cell collection device and method for obtaining tissue samples from the uterus of a patient. A number of devices have been developed to collect samples from the cervix including cotton swabs introduced into the uterine canal, wet spatulas, wooden spatulas, aspiration through plastic or glass pipettes, and endocervical sample collection brushes. Examples of such devices are disclosed in U.S. patents to MacLean (U.S. Pat. No. 2,955,591), Antonides (U.S. Pat. No. 3,626,470), Oster (U.S. Pat. No. 3,815,580), Vermes (U.S. Pat. No. 3,877,464), Levene (U.S. Pat. No. 3,881,464), Milan (U.S. Pat. No. 3,945,372), Nollan (U.S. Pat. No. 4,127,113), White (U.S. Pat. No. 4,175,008), Kist (U.S. Pat. No. 4,700,713), Bayne (U.S. Pat. No. 4,754,764), Bayne et al (U.S. Pat. No. 4,762,133), Bayne (U.S. Pat. Nos. 4,754,764 and 4,873,992), Bucaro (U.S. Pat. No. 4,862,899), Samuels (U.S. Pat. No. 4,953,560), Worthen et al. (U.S. Pat. No. 5,445,164), Sak (U.S. Pat. No. 5,787,891), Leet et al. (U.S. Pat. No. 5,795,309), and Wallach (U.S. Pat. Nos. 6,387,058 and 6,740,049)

Although cell collection brushes are well known and widely used, there are many disadvantages associated with the present cell collection brushes. One disadvantage is the dispersal of the collected biological material from the cell collection brushes into a sample vial. During use, a collection brush is inserted inside the vagina and is then rotated one or more full turns to scrape off tissue material from the opening of the endocervical canal. After the cell sample is collected, the collection brush is either swirled in a specimen vial containing cell preservative to release cells from the brush or a portion of the brush is detached into a specimen collection vial for transportation to a laboratory for processing.

A disadvantage associated with this type of brush assembly is that a number of cells remain attached to the collection brush even after the brush is agitated in solution. Since it is important to obtain a large enough sample of cells to ensure the chances of detecting abnormal cells in a sample, it would therefore be highly desirable to have a device which increases the total number of exocervical and endocervical cells collected from a patient.

SUMMARY OF THE INVENTION

The invention generally relates to medical devices, and more particularly, to medical devices and method for collecting cells or tissue samples from the uterus of a patient for medical testing. In one aspect of the present invention, a device for the collecting cells and other biological materials is presented. The medical device is comprised of a distal end portion for collecting cells, such distal end comprising a substantially porous tip; a proximal end portion comprising a pump; and an elongated middle portion comprising a lumen in fluid connection with the distal and proximal end portions and extending therethrough.

In another aspect of the invention, a medical device for collection biological material from a patient is provided. The medical device is comprised of a distal end portion for collecting cells, such distal end comprising a substantially porous tip; a proximal end portion comprising a pump; and an elongated middle portion comprising a lumen in fluid connection with the distal and proximal end portions and extending therethrough. The elongated middle portion of the medical device also contains at least one valve to prevent the uptake of fluid through the substantially porous tip and into the internal lumen of the elongated middle portion of the device.

In yet another aspect of the present invention, a method for collecting cells and other biological materials is presented. The method of collecting cells comprises collecting cells or other biological material using a device comprising a distal end portion for collecting cells with a substantially porous tip; a proximal end portion comprising a pump; and an elongated middle portion comprising a lumen in fluid connection with the distal and proximal end portions and extending therethrough, by drawing fluid into the lumen through the porous tip by creating negative pressure in the lumen by the pump; and expelling the fluid back through the lumen and out the porous distal tip by releasing the negative pressure. The expelling of the fluid back through the lumen and out the porous distal tip releases the collected cells from said the tip.

DETAILED DESCRIPTION

It is contemplated that embodiments of the present invention may be utilized for the collection of cells or tissue samples from the body of a patient for medical testing.

However, collection of cells or tissue samples from the uterus of a patient will be discussed below in an exemplary manner.

In one aspect of the present invention, a device for collecting cells and other biological materials is presented. The medical device is comprised of a distal end portion for collecting cells, such distal end comprising a substantially porous tip; a proximal end portion comprising a pump; and an elongated middle portion comprising a lumen in fluid connection with the distal and proximal end portions and extending therethrough.

According to a preferred embodiment, the substantially porous tip is comprised of an open cell flexible material such as foam or sponge. The foam may be comprised of polyolefin, urethane, polyurethane, or silicone materials. In a preferred embodiment of the present invention, the substantially porous tip is comprised of open cell foam.

The proximal end of the medical device includes an actuator for creating negative pressure at the distal tip thus drawing fluid through the substantially porous distal tip and into the lumen within the elongated middle portion of the device which is in fluid connection between the proximal and distal end portions of the device. In one embodiment of the present invention, the actuator for drawing a fluid through the substantially porous distal tip and into the lumen within the elongated middle portion of the device is a pump. In another embodiment of the present invention, the pump is an elastomeric retention bulb or a squeezable bladder.

The elongated portion of the present invention may be composed of glass or plastic. In one embodiment of the present invention, the medical device is composed plastic. Examples of plastics that may be used in the construction of the device include, for example, polypropylene, polystyrene, acrylonitrile-butadiene-styrene copolymer (ABS resin), polyethylene, polyvinyl chloride, polycarbonate, polyamide, and polyester.

In another embodiment of the present invention, a device for the collecting cells and other biological materials is presented. The collection device is comprised of a substantially porous distal end portion configured for collecting cells having a proximal end portion with an actuator coupled thereto; an elongated middle portion having a lumen in fluid connection with the distal and proximal end portions and extending therethrough.

Figure 1:
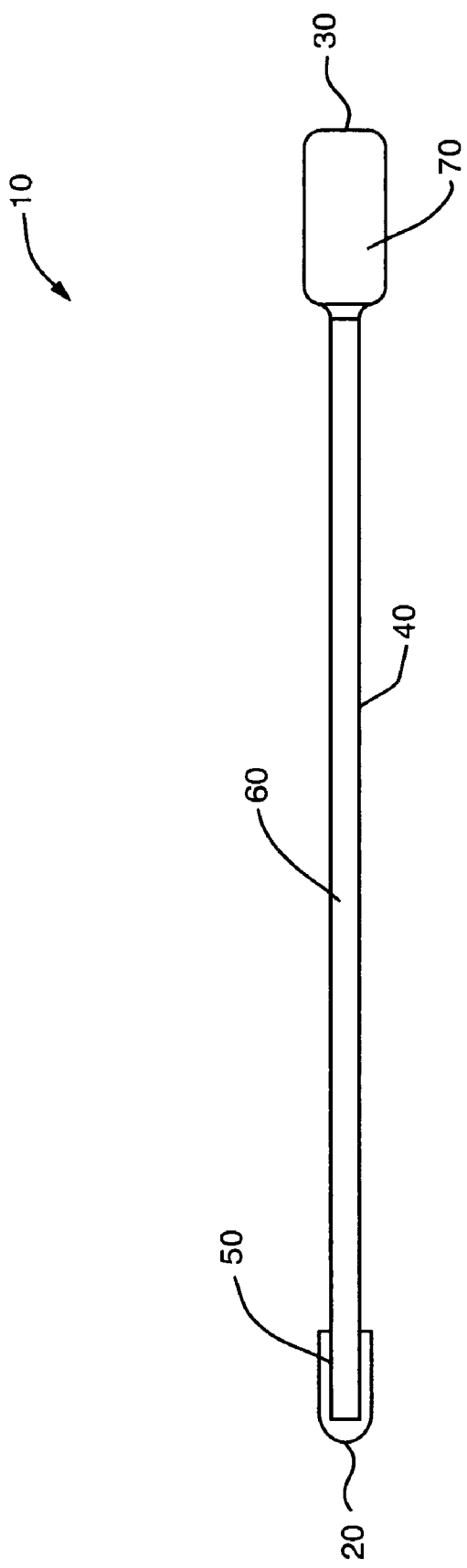
FIG. 1 is a side view of a first preferred embodiment of the present invention.

Referring first to FIG. 1 of the drawings, the collection device of the invention [10] includes a distal end portion [20] for collecting cells; a proximal end portion [30] including a pump [70]; and an elongated middle portion [40] comprising a lumen [60] in fluid contact with the proximal and distal end portions.

The distal end portion [20] of the collection device [10] has a substantially porous tip [14]. The proximal end portion [30] of the collection device [10] has a pump [70] for drawing fluid into the lumen [60] of the elongated middle portion [40] of the collection device. The proximal end portion [30] may be comprised of a flexible, squeezable bladder that is a separate assembly or molded as an integral part of the collection device.

The elongated middle portion [40] is comprised of a lumen [60] that is in fluid contact with both the proximal and distal end portions of the collection device. The lumen [60] has a bore of a sufficient diameter to allow unimpeded flow of fluid from the distal end portion [20] to the proximal end portion [30] of the collection device [10]. The elongated middle portion [40] has sufficient tensile strength to serve as a handle for the collection of biological material from a patient. The distal end of the elongated middle portion [40] of the collection device [10] may contain perforations which would allow the flow of fluid through the open cell foam tip [50] and into the lumen [60]. The size of the perforations is sufficient to prevent cells from entering the lumen of the collection device.

With the pump [70] in an uncompressed condition as shown in FIG. 1, the distal end portion [20] of the collection device [10] is inserted into the vagina of a patient (not shown). Insertion of the collection device [10] continues until the distal end portion [20] of the device contacts the cervix. Once the distal end portion [20] contacts the cervix, a specimen sample is obtained by swabbing the cervix with the open cell foam tip [50] of the collection device. Cells and other biological materials are captured on and within the open cell foam tip of the collection device. Once a specimen sample has been obtained, the collection device [10] is removed from the patient and the distal end portion [20] is placed into a specimen collection vial (nor shown) which contains a cell preservative solution. Rather than merely agitating the collection device in the preservative solution or depositing the collection portion of the device into fluid as is the current practice, the flexible squeezable bladder [70] or other similar pump may be activated, thus creating positive pressure which forces air through the lumen [60] of the elongated middle portion [40] of the collection device. When the flexible squeezable bladder [70] is released, negative pressure is created within the bladder which in turn draws fluid from the specimen collection vial through the porous open cell foam tip [50] and into the lumen [70] of the collection device. Subsequent activation of the pump [70] creates positive pressure which results in the expulsion of the fluid from lumen [70] through the porous open cell foam tip [50] and back into the specimen collection vial. The process may be repeated (several squeeze/release cycles). The movement of fluid through the foam tip aides in the dislodging of cells captured in and on the open pore material and into suspension within the fluid. The suspended cells may be used for further medical testing.

Another embodiment of the present invention, a one way valve is built into the shaft of the collection device near the foam tip. The valve is orientated such that when negative pressure is exerted by the bladder (releasing compression) fluid is drawn into the shaft. Additionally, another one-way valve is positioned within the shaft above the tip such that when negative pressure is exerted by the bladder (releasing compression), the valve closes thus preventing fluid from being drawn through the porous tip and into the lumen.

When positive pressure is exerted (by compressing the bladder), the valve closes. This allows fluid to be expelled from the collection device and not drawn into the device through the porous tip. The advantage of this embodiment of the invention is that a collection device may be pre-loaded with collection or preservative fluid before a specimen sample is collected from a patient. By pre-loading a collection device, the step of drawing fluid into the collection device, after a sample has been collected, may be avoided. Thus, a practitioner pre-loads the device, or obtains a pre-loaded collection device, by initially drawing fluid into the lumen through the porous tip by creating negative pressure in the lumen by the pump. The practitioner then collects a patient sample on the porous distal tip, inserts the distal tip into a specimen collection vial containing preservative solution, and then expels the fluid back through the lumen and out the porous distal tip by releasing the negative pressure. The expelling of the fluid back through the lumen and out the porous distal tip releases the collected cells from the tip and into suspension within the cell preservative solution in the specimen vial.

Figure 2:
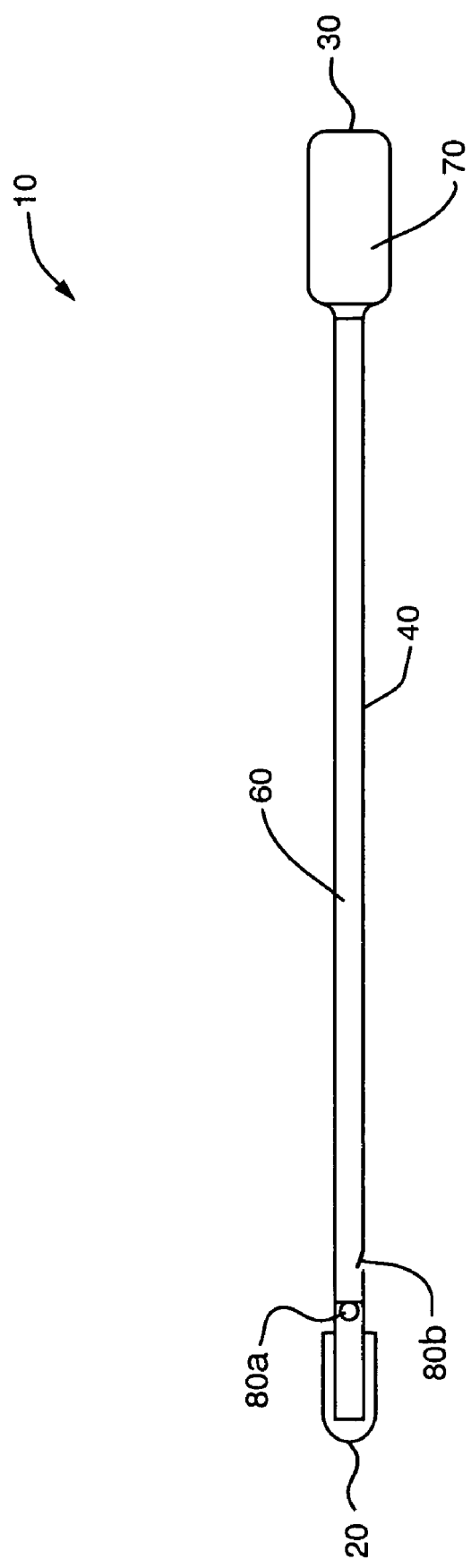
FIG. 2 is a side view of a second preferred embodiment of the present invention.

Referring now to FIG. 2 of the drawings, the collection device of the invention [10] includes a distal end portion [20] for collecting cells; a proximal end portion [30] comprising a pumping [70]; and an elongated middle portion [40] comprising a lumen [60] in fluid contact with the proximal and distal end portions. The elongated middle portion [40] contains at least one valve [80A; 80B] which prevent the flow of fluid from the distal end portion [20] to the proximal end portion [30] of the collection device [10].

In another aspect of the present invention, a method for collecting cells and other biological materials is presented. The method of collecting cells comprises collecting cells or other biological material using a device comprising a distal end portion for collecting cells with a substantially porous tip; a proximal end portion comprising a pump; and an elongated middle portion comprising a lumen in fluid connection with the distal and proximal end portions and extending therethrough, by drawing fluid into the lumen through the porous tip by creating negative pressure in the lumen by the pump; and expelling the fluid back through the lumen and out the porous distal tip by releasing the negative pressure. The expelling of the fluid back through the lumen and out the porous distal tip releases the collected cells from said tip and into the collection fluid. The suspended cells may be further processed for medical testing or visual examination such as liquid based cytology. Examples of methods and apparatus for generating a thin monolayer of cells on a slide advantageous for visual examination are disclosed in U.S. Pat. No. 5,143,627 issued to Lapidus et al. and entitled "Method and Apparatus for Preparing Cells for Examination;" U.S. Pat. No. 5,240,606 issued to Lapidus et al. and entitled "Apparatus for Preparing Cells for Examination;" U.S. Pat. No. 5,269,918 issued to Lapidus et al. and entitled "Clinical Cartridge Apparatus;" U.S. Pat. No. 5,282,978 issued to Polk, Jr. et al. and entitled "Specimen Processor Method and Apparatus," and U.S. Pat. No. 6,572,824 issued to Ostgaard et al. and entitled "Method and Apparatus for Preparing Cytological Specimens;" all of which are assigned to the assignee of the present invention and all of the disclosures of which are incorporated herein by reference in their entirety.

In yet another aspect of the present invention, a method for collecting cells and other biological materials is presented. The method of collection cells comprises inserting a collection device into a patient's vagina wherein the collection device is comprised of a substantially porous distal end portion configured for collecting cells; a proximal end portion having a pump coupled thereto; and an elongated middle portion having a lumen in fluid connection with said distal and proximal end portions and extending therethrough. Once the collection device has been inserted into a patient's vagina and is positioned near the patient's cervix, a biological sample is obtained by swabbing or wiping the patient's cervix with the substantially porous distal end of the collection device.

Once the biological sample has been obtained, the collection device is removed from the patient's vagina and the substantially porous distal end of the collection device is inserted into a specimen vial containing collection fluid such that the distal end of the collection device is submerged in the collection fluid. The collection fluid may consist of a cell preservative fluid or any other fluids used for the preservation, processing, or storage of biological samples for future medical testing or evaluation.

Once submerged, fluid from the specimen collection vial is drawn into the lumen of the collection device through the substantially porous distal tip by creating negative pressure in the lumen by an actuator. The actuator may be any device that is capable of creating positive or negative pressure within the lumen of the collection device such as a pump.

After fluid has been drawn into the lumen, fluid is then expelled back through the lumen and out of the substantially porous distal end by releasing the negative pressure. The process of expelling fluid back through the lumen and out of the substantially porous distal tip releases the collected cells from the porous distal tip and into the collection fluid.

In still yet another aspect of the present invention, a method for collecting cells and other biological materials is presented. The method of collection cells comprises using a collection device which is comprised of a substantially porous distal end portion configured for collecting cells; a proximal end portion having a actuator, such as a pump, coupled thereto; at least one, one-way valve built into the elongated portion of the collection device near the foam tip; and an elongated middle portion having a lumen in fluid connection with the distal and proximal end portions and extending therethrough. An example of a pump is an elastomeric retention bulb or bladder. The one-way valve is orientated such that when negative pressure is exerted by the pump (releasing compression) fluid is drawn into the lumen. Additionally, another one-way valve is positioned within the elongated portion of the collection device above the tip such that when negative pressure is exerted by the pump (releasing compression), the valve closes thus preventing fluid from being drawn through the porous tip and into the lumen. When positive pressure is exerted by the pump, the valve closes. This allows fluid to be expelled from the collection device and not drawn into the device through the porous tip.

Thus, a practitioner pre-loads the collection device, or obtains a pre-loaded collection device, by initially drawing fluid from the specimen collection vial into the lumen of the collection device before collecting the patient sample. Examples of fluid would be preservative fluids or other collection fluids. After the collection device has been pre-loaded, the practitioner then collects a patient sample by inserting the collection device into a patient's vagina. Once the collection device is inserted into a patient's vagina and is positioned near the patient's cervix, a biological sample is obtained by swabbing or wiping the patient's cervix with the substantially porous distal end of the collection device.

After a biological sample has been obtained, the collection device is removed from the patient's vagina and the substantially porous distal end of the collection device is inserted into a specimen vial containing collection fluid which is substantially similar or identical to the fluid pre-loaded into the collection device, such that the distal end of the collection device is submerged in the collection fluid. The collection fluid may consist of a cell preservative fluid or any other fluids used for the preservation, processing, or storage of biological samples for future medical testing or evaluation.

Once submerged, the collection device may be agitating in the collection fluid to dislodge cells of other biological material captured on or in the porous distal tip. To further dislodge any remaining cells or other biological material that may remain in the porous distal tip of the collection device, fluid pre-loaded into the lumen of the device may be expelled back through the lumen and out of the substantially porous distal end by applying positive pressure by the actuator. The process of expelling fluid back through the lumen and out of the substantially porous distal tip releases any remaining collected cells from the porous distal tip and into the collection fluid.

The invention can be embodied in other specific forms without departing from the spirit or essential characteristics thereof. The present embodiments are therefore to be considered in all respects as illustrative and not restrictive. The scope of the invention is indicated by the appended claims, rather than by the foregoing description, and all changes which come within the meaning and range of equivalency of the claims are therefore intended to be embraced therein.

The invention claimed is:

1. A method for collecting cells and other biological materials, comprising:
   inserting a collection device into a patient's vagina wherein the collection device is comprised of:
      a substantially porous distal end portion configured for collecting cells; a proximal end portion having a pump coupled thereto; and an elongated middle portion having a lumen in fluid connection with said distal and proximal end portions and extending therethrough;
   wiping the patient's cervix with the substantially porous distal end of the collection device to collect a biological sample;
   removing the collection device from the patient's vagina;
   inserting the substantially porous distal end of the collection device into a specimen vial containing collection fluid;
   drawing fluid into the lumen of the collection device through the substantially porous distal tip by creating negative pressure in the lumen by an actuator; and
   expelling the fluid back through the lumen and out of the substantially porous distal end by releasing the negative pressure;
   wherein expelling the fluid back through the lumen and out of the substantially porous distal tip releases the collected cells from the porous distal tip and into the collection fluid.

2. The method according to claim 1, wherein said actuator comprises an elastomeric retention bulb.

3. The method according to claim 1, wherein said biological sample comprises ectocervical cells.

4. The method according to claim 1, wherein said substantially porous tip is comprised of an open cell foam material.

5. The method according to claim 1, wherein said distal and proximal end portions are integrally molded with said elongated middle portion.

* * * * *